US00PP30681P3

(12) United States Plant Patent
Suphachadiwong

(10) Patent No.: US PP30,681 P3
(45) Date of Patent: Jul. 9, 2019

(54) *VANDA* PLANT NAMED 'SPCDW1703'

(50) Latin Name: *Vanda* spp. Jones ex R. Br.
Varietal Denomination: SPCDW1703

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 15/998,366

(22) Filed: Aug. 9, 2018

(65) Prior Publication Data

US 2019/0053413 P1 Feb. 14, 2019

(30) Foreign Application Priority Data

Aug. 9, 2017 (QZ) ..... PBR 2017/1983

(51) Int. Cl.
*A01H 5/02* (2018.01)
*A01H 6/62* (2018.01)

(52) U.S. Cl.
USPC ..... Plt./311
CPC ..... *A01H 6/62* (2018.05); *A01H 5/02* (2013.01)

(58) Field of Classification Search
USPC ..... Plt./311
CPC ..... A01H 5/02
See application file for complete search history.

*Primary Examiner* — Kent L Bell
(74) *Attorney, Agent, or Firm* — Samuel R. McCoy, Jr.

(57) ABSTRACT

A new and distinct *Vanda* plant named 'SPCDW1703' which is characterized by large flowers with light red-purple petals and sepals that are reticulated and dotted dark red-purple, lateral petals with lightly to moderately undulated margins, a labellum with a very dark red-purple central lobe and light yellow lateral lobes which are lightly striped with dark purple, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1703'.

CROSS REFERENCE TO RELATED APPLICATIONS

This application claims priority to the Community Plant Variety Rights application number 2017/1983, filed Aug. 9, 2017, which is herein incorporated by reference.

BACKGROUND OF THE INVENTION

Parentage: The *Vanda* variety 'SPCDW1703' is the result of a planned breeding program. The new variety originated as a seedling from the crossing of *Vanda* 'A77' (not patented), the seed parent, with *Vanda* 'SJ60' (not patented), the pollen parent. Both parents were developed by, and are owned by, the inventor and were never commercially released. The crossing was made by the inventor in his research greenhouse in Bangphra, Thailand in December of 1994.

The new variety was first selected in February of 1999, in a research greenhouse in Bangphra, Thailand belonging to the inventor. After identifying the new variety as a potentially interesting selection, the inventor continued confidential testing and propagation of 'SPCDW1703', assessing stability of the unique characteristics of this variety.

Asexual Reproduction: Asexual reproduction of the new cultivar 'SPCDW1703', by way of mericloning, was first initiated in October of 2010 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1703' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1703'. These characteristics in combination distinguish 'SPCDW1703' as a new and distinct *Vanda* cultivar:

1. *Vanda* 'SPCDW1703' exhibits numerous large flowers borne on an inflorescence carried slightly above the foliage; and
2. *Vanda* 'SPCDW1703' exhibits light red-purple lateral petals which are heavily dotted dark red-purple; and
3. *Vanda* 'SPCDW1703' exhibits lateral petals with lightly to moderately undulated margins; and
4. *Vanda* 'SPCDW1703' exhibits a light red-purple dorsal sepal which is overlaid with dark red-purple reticulation and dotting; and 5. *Vanda* 'SPCDW1703' exhibits light red-purple laterals sepals which are overlaid with a dark red-purple reticulate color pattern; and
6. *Vanda* 'SPCDW1703' exhibits a labellum with a very dark red-purple central lobe, and light yellow lateral lobes which are lightly striped with dark purple.

BOTANICAL DESCRIPTION OF THE PLANT

Figure 1:
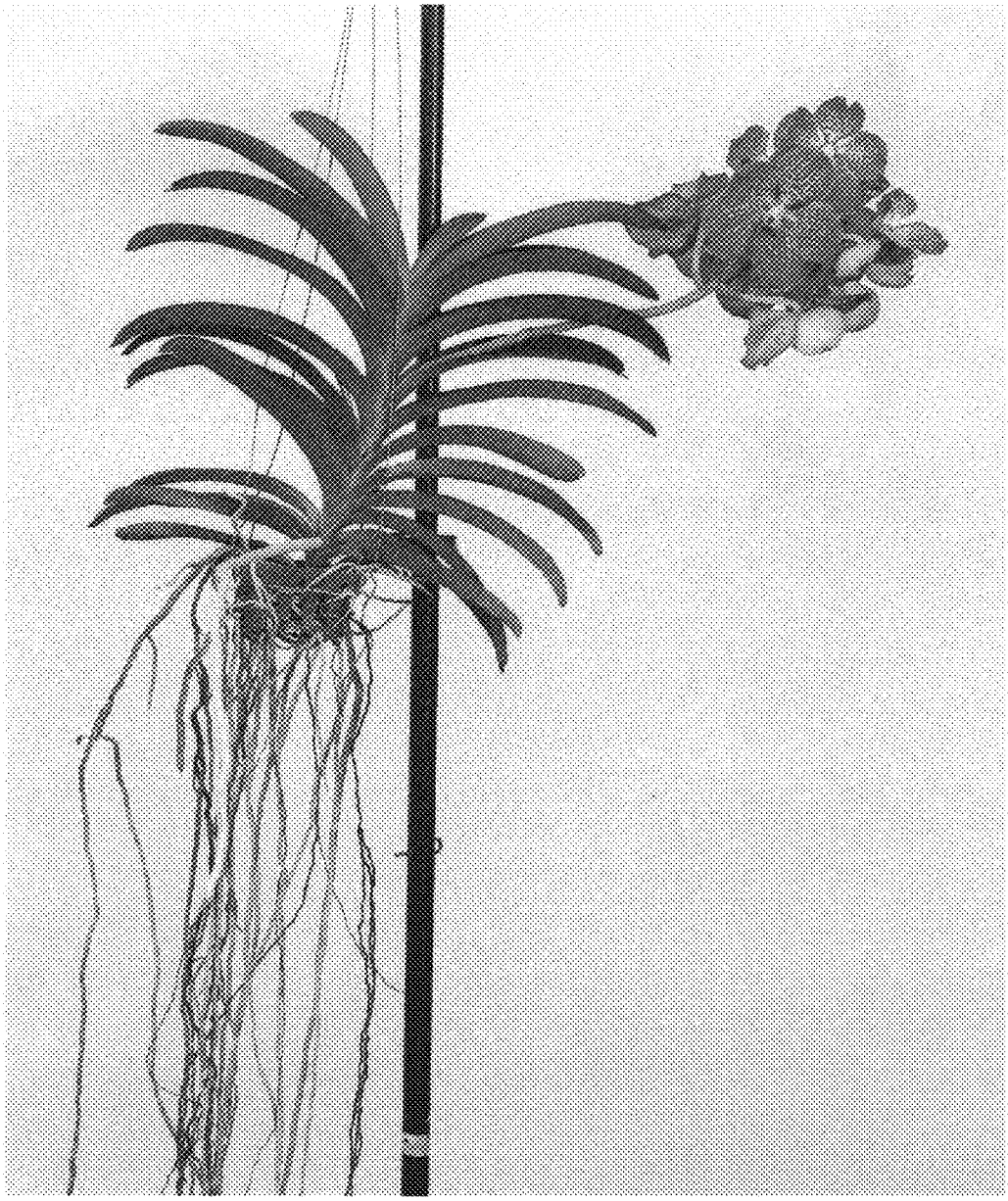
FIG. 1 illustrates, as nearly true as it is reasonably possible to make the same in color photographs of this type, an exemplary plant of 'SPCDW1703' grown in a commercial greenhouse in Honselersdijk, the Netherlands. This plant is approximately 6 years old from the time of mericloning, shown planted in an 8 by 8 cm container.
Figure 2:
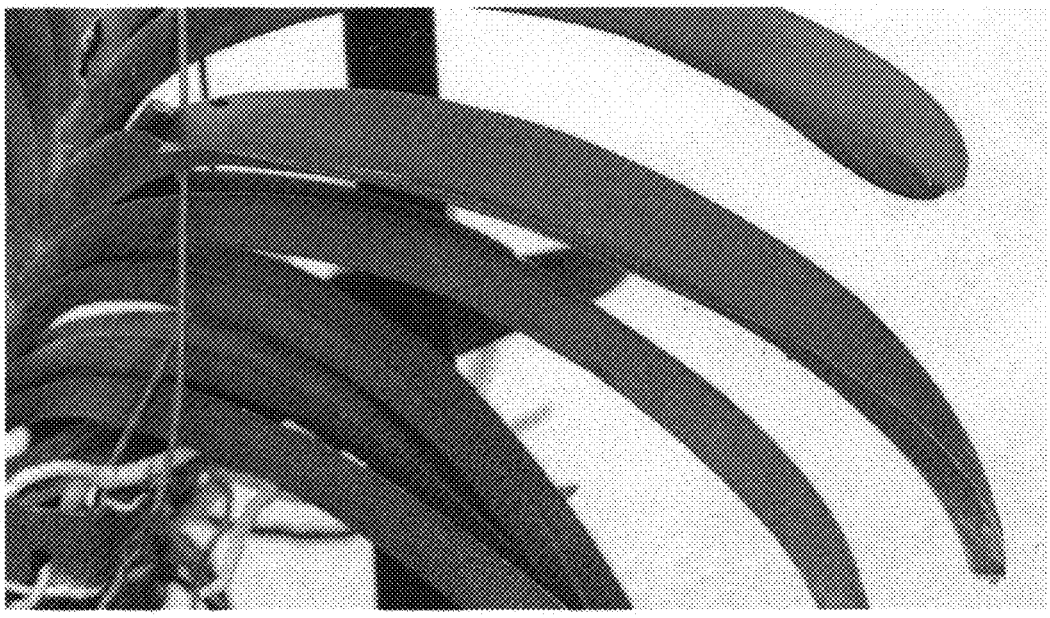
FIG. 2 illustrates, as nearly true as it is reasonably possible to make the same in color photographs of this type, the typical foliage of 'SPCDW1703'.
Figure 3:
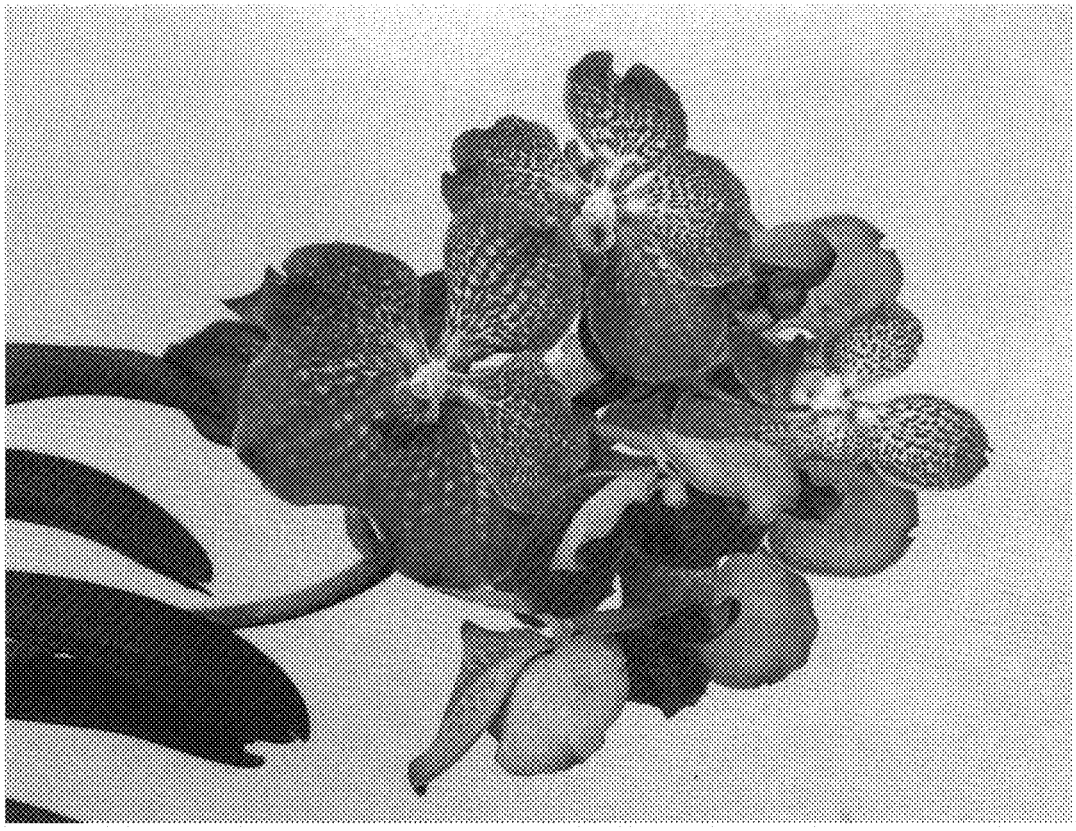
FIG. 3 illustrates, as nearly true as it is reasonably possible to make the same in color photographs of this type, the typical inflorescence of 'SPCDW1703'.
Figure 4:
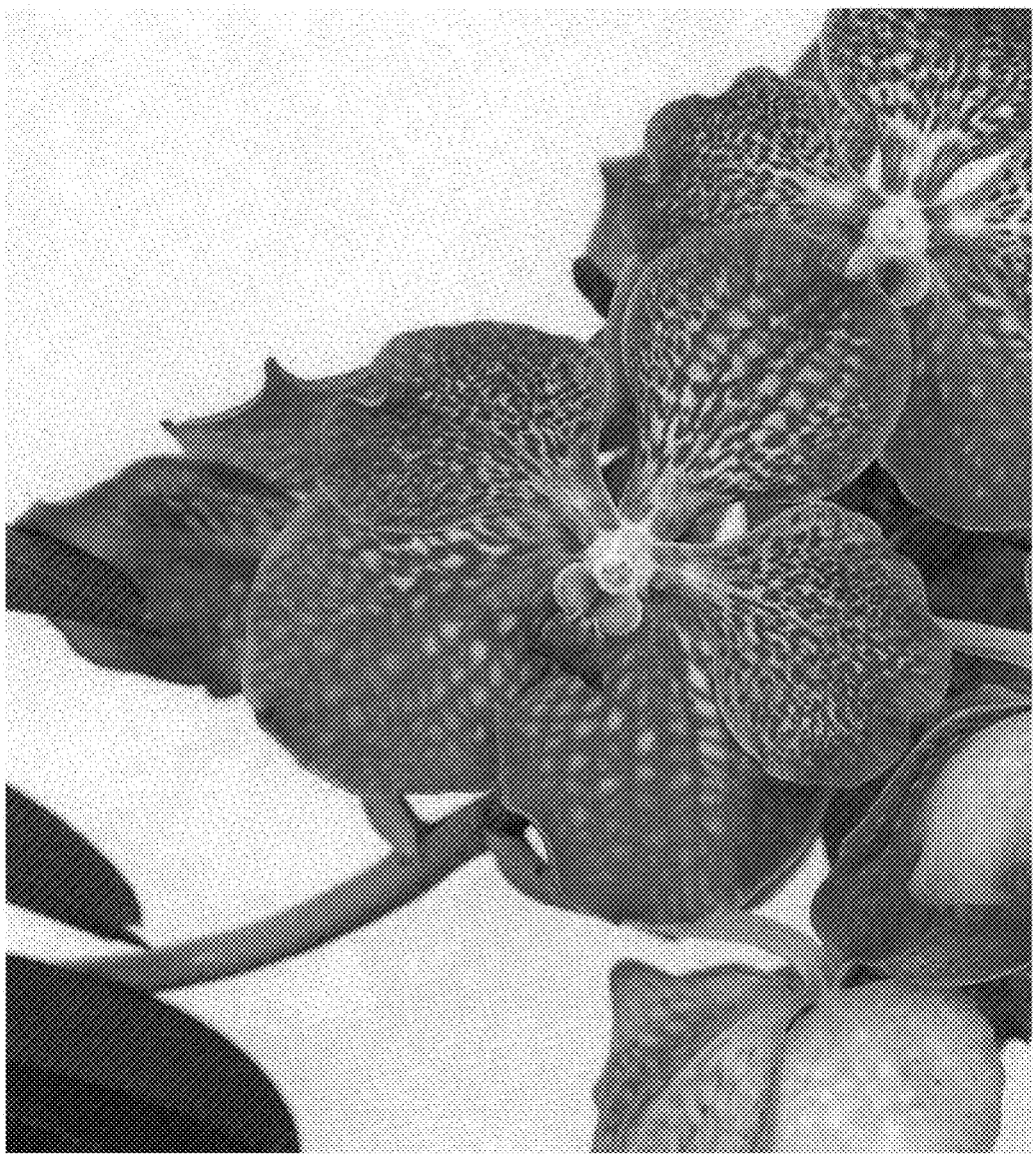
FIG. 4 illustrates, as nearly true as it is reasonably possible to make the same in color photographs of this type, the typical flower of 'SPCDW1703'.

The following observations and measurements made in August of 2018 describe averages from a sample set of six specimens of six year-old 'SPCDW1703' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1703' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1703' and comparisons with the parents and most similar commercial variety of *Vanda* are provided below.

Plant description:

*Growth habit*.—Perennial; monopodial, upright. Single monopodial leafy stem, with flowers carried slightly above the leaf plane; inflorescences growing from the leaf axils.

*Average height from base (plant grown in hanging basket, so no soil line present) to foliar plane*.—33.6 cm.

*Average height from base (plant grown in hanging basket, so no soil line present) to top of floral plane*.—42.0 cm.

*Plant spread*.—Average of 57.7 cm.

*Appropriate container size*.—8 cm by 8 cm rectangular hanging basket.

*Growth rate*.—Moderate.

*Plant vigor*.—Moderate.

*Propagation type*.—Meristematic tissue culture propagation using the base of the leaves.

*Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility*.—Plants have not been observed to be susceptible or resistant to pathogens and pests common to *Vanda*.

*Environmental tolerances*.—Adapt to, at least, USDA Zones 11 and 12 and temperatures as high as 40 degrees Celsius; high tolerance to rain; moderate to high tolerance to wind.

Root system:

*General*.—Moderately to densely rooting; with aerial roots only.

*Dimensions, mature roots*.—105.3 cm long with a diameter of 0.45 cm, on average.

*Texture*.—Very fleshy; non-fibrous.

*Color*.—Greyed-green, nearest to RHS 193B; root apex is yellow-green, RHS 148A.

Stem:

*Branching habit*.—Monopodial; no lateral branches present.

*Number of primary (main) stems per plant*.—One.

*Number of secondary (lateral) branches per plant*.—None.

*Appearance and shape*.—Circular, formed by the leaf sheaths.

*Length*.—21.0 cm.

*Diameter*.—0.9 cm.

*Internode length*.—1.0 cm.

*Luster*.—Matte.

*Aspect, main stem*.—Near vertical.

*Strength*.—Very strong.

*Color, juvenile*.—Yellow-green, nearest to RHS 145D.

*Color, mature*.—In between yellow-green, RHS 153D, and greyed-yellow, RHS 162D.

*Color at internodes*.—In between yellow-green, RHS 153D, and greyed-yellow, RHS 162D.

*Pubescence*.—Glabrous.

Foliage:

*Arrangement*.—Distichous.

*Dimensions*.—20.2 cm long, excluding the sheath, and 2.7 cm wide.

*Shape of blade*.—Ligulate; moderately to strongly carinate.

*Aspect*.—Moderately curved.

*Apex*.—Unequal praemorse.

*Base*.—Sheathing.

*Sheath dimensions*.—3.8 cm long and 1.2 cm wide, on average.

*Sheath color*.—Yellow-green, nearest to in between RHS 145A and 145B.

*Margin*.—Entire.

*Pubescence, texture and luster of adaxial surface*.—Glabrous, smooth, and matte.

*Pubescence, texture and luster of abaxial surface*.—Glabrous, smooth, and matte.

*Color*.—Juvenile foliage, adaxial surface — Green, nearest to RHS 143A; darker towards the apex and margins, nearest to RHS 137A. Juvenile foliage, abaxial surface — Green, nearest to RHS 143A; darker towards the apex and margins, nearest to RHS 137B. Mature foliage, adaxial surface — Green, nearest to RHS NN137B. Mature foliage, abaxial surface — Nearest to in between green, RHS 143A, and yellow-green, RHS 144A.

*Venation*.—Pattern — Parallel. Color, adaxial surface — Green, nearest to RHS 139A. Color, abaxial surface — Yellow-green, nearest to RHS 144C.

*Petiole*.—No petioles present; leaves sessile.

Inflorescence:

*Inflorescence arrangement*.—Axially placed raceme.

*Natural flowering season*.—Autumn into winter.

*Time to flower*.—Approximately 10 months.

*Flowers per inflorescence*.—Average of 14.

*Flowers per plant*.—13 open flowers and 1 flower buds.

*Inflorescence height*.—Approximately 22.0 cm (measured from base of lowest flower to top of upper flower).

*Inflorescence diameter*.—Approximately 18.2 cm.

*Peduncle*.—Dimensions — Approximately 37.4 cm long and 0.7 cm wide. Aspect — Generally at a 30 degree angle to lateral branch axis. Strength — Moderately strong. Texture and luster — Glabrous and matte. Color — Yellow-green, nearest to RHS 144A.

Bud:

*Length*.—Average of 1.6 cm.

*Diameter*.—Average horizontal diameter is 1.8 cm; the vertical diameter is 2.2 cm.

*Shape*.—Cubic, with a deltoid apex which is pointed downward.

*Pubescence, texture and luster*.—Glabrous, smooth and matte.

*Color*.—In between purple, RHS N77B, and greyed-purple, RHS 186A, and fading to greyed-green towards the base, nearest to RHS 195D; apex is greyed-purple, nearest to RHS 186D; bud is sparsely dotted purple, nearest to RHS N77A.

Flower:

*Flower type*.—Zygomorphic (orchidaceous), typical shape for the genus *Vanda*.

*Flowering habit*.—Moderately free flowering.

*Shape*.—Zygomorphic, single; consisting of three sepals and three petals, one of which is transformed into a labellum; the two lateral petals slightly to moderately overlap the lateral sepals and touching the dorsal sepal; lateral sepals slightly overlap one another.

*Attitude*.—Flowers are outward-facing to slightly nodding.

*Vertical height*.—Approximately 9.9 cm.

*Diameter*.—Approximately 9.3 cm.

*Depth*.—Approximately 3.4 cm.

*Fragrance*.—No fragrance.

*Lastingness*.—3 weeks, on average.

*Persistent*.—Self-cleaning.

*Petals*.—Quantity of Petals — Three unfused petals; two conventional petals and one labellum. Arrangement — One lateral petal on each side. Length — Approximately 4.5 cm. Width — Approximately 4.2 cm. Shape — Broad obovate. Apex — Obtuse. Base — Cuneate. Margin — Entire; lightly to moderately undulated. Pubescence, texture and luster of upper surface — Glabrous, velvety and matte. Pubescence, texture and luster of lower surface — Glabrous, velvety and matte. Color when opening, upper surface — White, nearest to RHS 155B, and heavily suffused with greyed-purple, and more so towards the margins and apex, nearest to RHS 186B; heavily dotted greyed-purple, nearest to a mixture of RHS 186B, 186C, and N187C; base of the petal is greyed-purple, nearest to RHS 187A. Color when opening, lower surface — White, nearest to RHS NN155D, and heavily suffused with greyed-purple towards the margins and apex, nearest to RHS 186C. Color when fully opened, upper surface — White, nearest to RHS NN155C, and heavily suffused with red-purple, and more so towards the margins and apex, nearest to a mixture of RHS 64A and 64B; heavily dotted red-purple, nearest to a mixture of RHS 60B, 61A, and 64C; base of the petal is greyed-purple, nearest to RHS 185B. Color when fully opened, lower surface — White, nearest to RHS N155A, and suffused with green-white, nearest to RHS 157D; heavily suffused with red-purple towards the margins and apex, nearest to a mixture of RHS 72B and 72C. Fading, upper surface — Not fading. Fading, lower surface — Not fading. Venation — Densely reticulate on the upper surface; only the main vein is visible on the lower surface. Venation color, fully opened, upper surface — White, nearest to RHS NN155C, and suffused with red-purple, and more so towards the margins and apex, nearest to a mixture of RHS 64A and 64B; heavily dotted red-purple, nearest to a mixture of RHS 60B, 61A, and 64C; base of the petal is greyed-purple, nearest to RHS 185B. Venation color, fully opened, lower surface — Only the main vein is visible; colored red-purple, nearest the RHS 72C.

*Labellum*.—Shape — Three-lobed; the shape of the lateral lobes is obovate, and the aspect is involute; the shape of the central lobe is broad obovate to oblong, and the aspect is slightly revolute. Length — Central lobe — Approximately 1.8 cm. Lateral lobes — Approximately 0.7 cm. Width — Central lobe — Approximately 0.8 cm at the base; 1.2 at the apex. Lateral lobes — Approximately 0.7 cm. Apex — Central lobe — Emarginate. Lateral lobes — Emarginate. Base — Central lobe — Cuneate. Lateral lobes — Cuneate. Margin — Central lobe — Entire; lightly undulated. Lateral lobes — Entire; not undulated. Texture and luster of upper surface — Central lobe — Glabrous, velvety, and matte. Lateral lobes — Glabrous, velvety, and matte. Texture and luster of lower surface — Central lobe — Glabrous, velvety, and matte, except for the apex which is moderately glossy. Lateral lobes — Glabrous, velvety, and matte. Color when opening, upper surface — Central lobe — Red-purple, nearest to RHS 71A, and fading to a lighter shade of red-purple towards the base, nearest to RHS 72C. Lateral lobes — Yellow-green, nearest to RHS 150D. Color when opening, lower surface — Central lobe — Purple, nearest to RHS 75D, and becoming red-purple, nearest the RHS 71A, at the upper one-third portion of the lobe. Lateral lobes — Yellow-green, nearest to RHS 150D. Color when fully opened, upper surface — Central lobe — Nearest to in between red-purple, RHS 71A, and purple, RHS N79B, and fading to a lighter shade of red-purple towards the base, nearest the RHS 71A. Lateral lobes — Yellow-green, nearest to RHS 150D, and suffused with yellow at the apex, nearest the RHS 5C; lightly striped red-purple, nearest to RHS 70C. Color when fully opened, lower surface — Central lobe — Purple, nearest to RHS 75D, and becoming a dark shade of purple at the upper one-third portion of the lobe, nearest the RHS N79B. Lateral lobes — Yellow-green, nearest to RHS 150D, and lightly striped red-purple, nearest to RHS 70D. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities*.—Dimensions — 1.3 cm long and 0.6 cm wide, on average. Color — Red-purple, nearest to RHS 71A, and fading to a lighter shade of red-purple towards the base, nearest to a mixture of RHS 72B and 72C.

*Spurs*.—Quantity — Average of 1. Length — Approximately 0.7 cm. Diameter — Approximately 0.3 cm. Vertical height — Approximately 0.6 cm, at the base. Shape — Short triangular; flattened. Apex — Bluntly acute. Base — Broad cuneate. Pubescence, texture and luster — Glabrous, smooth, and matte. Color — White, nearest to RHS 155C, and radially striped purple, nearest to RHS 75B.

*Sepals*.—Quantity — Average of 3 unfused sepals. Arrangement — One dorsal sepal and two lateral sepals. Length — Dorsal sepal — Approximately 4.7 cm. Lateral sepals — Approximately 5.3 cm. Width — Dorsal sepal — Approximately 4.2 cm. Lateral sepals — Approximately 4.8 cm. Shape — Dorsal sepal — Broad obovate. Lateral sepals — Broad obovate. Apex — Dorsal sepal — Obtuse. Lateral sepals — Obtuse. Base — Dorsal sepal — Cuneate. Lateral sepals — Cuneate. Margin — Dorsal sepal — Entire; lightly undulated. Lateral sepals — Entire; lightly undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — White, nearest to RHS 155B, and heavily suffused with red-purple, and more so towards the apex, nearest to RHS 64B; base of the sepal is greyed-purple, nearest to a mixture of RHS 184B and 184C. Sepal is heavily dotted greyed-purple, nearest to a mixture of RHS 186B, 186C, and N187C. Lateral sepals — Greyed-purple, nearest to a mixture of RHS 186B and 186C, and fading to yellow-green towards the base, nearest the RHS 150D. Sepal is veined greyed-purple, RHS 186A. Color when opening, lower surface — Dorsal sepal — White, nearest to RHS NN155D, and heavily suffused with red-purple, even more so towards the margins and apex, nearest to RHS 64C. Lateral sepals — Greyed-green, nearest to RHS 169C, and suffused with red-purple, more so towards the margins and apex, nearest to a mixture of RHS 64B and 64C. Sepal is sparsely dotted red-purple, nearest to RHS 63B. Color when fully opened, upper surface — Dorsal sepal — White, nearest to RHS NN155C, and heavily suffused with red-purple, and more so towards the margins and apex, nearest to a mixture of RHS 64A and 64B; base of the sepal is greyed-purple, nearest to RHS 185C. Sepal is heavily dotted with red-purple, nearest to a mixture of RHS 60B, 61A, and 64C. Lateral sepals — Yellow-green, nearest to RHS 150D, and heavily suffused with red-purple, and more so towards the margins and apex, nearest to a mixture of RHS 64A and 64B. Color when fully opened, lower surface — Dorsal sepal — Purple, nearest to RHS 76C, and suffused with pink towards the margins and apex, nearest to a mixture of RHS NN74A and NN74B. Sepal is sparsely dotted red-purple, nearest to a mixture of RHS 72A and 72B. Lateral sepals — Greyed-green, nearest to RHS 169C, and suffused with red-purple towards the margins and apex, nearest to a mixture of RHS 70A and 70B. Fading, upper surface — Not fading. Fading, lower surface — Not fading. Venation — Densely reticulate. Venation color, fully opened, upper surface — Dorsal sepal — White, nearest to RHS NN155C, and suffused with red-purple, and more so towards the margins and apex, nearest to a mixture of RHS 64A and 64B; base is greyed-purple, nearest to RHS 185C. Heavily dotted with red-purple, nearest to a mixture of RHS 60B, 61A, and 64C. Lateral sepals — Greyed-purple, nearest to RHS N186D. Venation color, fully opened, lower surface — Dorsal sepal — Purple, nearest to RHS 76B. Lateral sepals — Red-purple, nearest to RHS 71B.

*Pedicels*.—Length — Approximately 5.2 cm. Diameter — Approximately 0.4 cm. Angle — Approximately 80 degree angle to peduncle axis. Strength — Moderate. Texture — Glabrous, axially angled with 5 "ribs", axially twisted (due to resupination). Luster — Moderately glossy. Color — Purple, nearest to RHS 77B, and becoming greyed-purple towards the proximal end, nearest to RHS 181D.

*Bract*.—Quantity — One bract present at the base of each pedicel. Shape — Broad oblong; folded around the base of each pedicel. Dimensions — Average of 1.8 cm long and 1.0 cm wide. Apex — Broad obtuse. Base — Broad cuneate. Margins — Entire. Color, inner surface — Yellow-green, nearest to RHS 144B. Color, outer surface — Yellow-green, nearest to RHS 144B.

Reproductive organs:

*Column*.—Length — Approximately 0.6 cm. Diameter — Approximately 0.7 cm. Color — White, nearest to RHS 155B; the upper surface is suffused with purple, nearest the RHS 77C.

*Ovary*.—Position — Inferior. Diameter — Approximately 0.2 cm. Color — Green-white, nearest to RHS 157D.

*Pollinia color*. 13 Yellow-orange, nearest to RHS 14B.

Seed and fruit: No fruit and seed production has been detected to date.

COMPARISON WITH THE PARENT PLANTS

Plants of the new cultivar 'SPCDW1703' differ from the *Vanda* seed parent, 'A77' (not patented), by the characteristics described in Table 1.

TABLE 1

| Characteristic | 'SPCDW1703' | 'A77' |
|---|---|---|
| Vigor; rate of growth. | Slower growing than 'A77'. | Faster growing than 'SPCDW1703'. |
| Flowering habit. | More freely flowering. | Less freely flowering. |
| Inflorescence length. | Longer than 'A77'. | Shorter than 'SPCDW1703'. |
| Flower size. | Larger than 'A77'. | Smaller than 'SPCDW1703'. |
| General coloration of the petals and sepals (excluding the overlaid color pattern) when fully opened. | White and suffused with red-purple. | White and suffused with blue. |

Plants of the new cultivar 'SPCDW1703' differ from the *Vanda* pollen parent, *Vanda* 'SJ60' (not patented), by the characteristics described in Table 2.

TABLE 2

| Characteristic | 'SPCDW17031' | 'SJ60' |
|---|---|---|
| Vigor; rate of growth. | Easier to propagate and faster growing than 'SJ60'. | More difficult to propagate and slower growing than 'SPCDW1703'. |
| Peduncle strength. | Stronger than 'SJ60'. | Weaker than 'SPCDW1703'. |
| Flower size. | Larger than 'SJ60'. | Smaller than 'SPCDW1703'. |

TABLE 2-continued

| Characteristic | 'SPCDW17031' | 'SJ60' |
|---|---|---|
| General coloration of the petals and sepals (excluding the overlaid color pattern) when fully opened. | White and suffused with red-purple. | White and suffused with violet-blue. |

COMPARISON WITH THE MOST SIMILAR *VANDA* CULTIVAR KNOWN TO THE INVENTOR

Plants of the new cultivar 'SPCDW1703' are similar to the cultivar, *Vanda* 'SPCDW1512' (European Community Plant Variety Rights grant number 45556). A comparison of 'SPCDW1703' with *Vanda* 'SPCDW1512' is described in Table 3.

TABLE 3

| Characteristic | 'SPCDW1703' | 'SPCDW1512' |
|---|---|---|
| Flower petal arrangement. | Less overlapping. | More overlapping. |
| Petal undulation. | More heavily undulated. | Not as undulated. |
| General coloration of the lateral sepals and petals when fully opened (excluding the overlaid color pattern). | White and suffused with red-purple. | White and more heavily suffused with red-purple. |
| Occurrence of spotting on the lateral petals. | Fewer spots. | More spots. |
| Overlaid color pattern of the sepals. | More reticulated than spotted. | More spotted than reticulated. |
| Width of the central lobe of the labellum. | More narrow than 'SPCDW1512'. | Wider than 'SPCDW1703'. |

That which is claimed is:

1. A new and distinct variety of *Vanda* plant named 'SPCDW1703', substantially as described and illustrated herein.

* * * * *